United States Patent [19]

Hakim et al.

[11] 3,975,388

[45] Aug. 17, 1976

[54] PYRIDAZINONES

[75] Inventors: Mehmood Abdulhameed Hakim; Peter Thomas Bysouth, both of Edinburgh, Scotland

[73] Assignee: BDH Pharmaceuticals Limited, Edinburgh, Scotland

[22] Filed: Nov. 11, 1974

[21] Appl. No.: 522,538

Related U.S. Application Data

[63] Continuation of Ser. No. 225,270, Feb. 10, 1972, abandoned.

[30] Foreign Application Priority Data

Feb. 22, 1971 United Kingdom............... 5082/71

[52] U.S. Cl.................. 260/250 A; 260/247.2 A; 260/239 BA; 260/268 C; 260/268 PH; 260/293.8; 260/295 R; 260/326.41; 260/473 R; 260/521 R; 260/519; 260/247.2 R; 424/248; 424/250

[51] Int. Cl.²...................................... C07D 237/04

[58] Field of Search............................. 260/250 A

[56] References Cited

FOREIGN PATENTS OR APPLICATIONS

| | | | |
|---|---|---|---|
| 2,207,517 | 12/1972 | Germany | 260/250 A |
| 696,254 | 8/1953 | United Kingdom | 260/250 A |

OTHER PUBLICATIONS

Nour et al., Pyridazines, Part I, The Synthesis of 6-aryl-4,5-dihydro-3 hydroxy-4-pyridazinylideneglycollohydrazides, Journal of Chemical Society 1964 (Dec.) 5302–5306.

Berichte, 1899, 32, pp. 395–409.

*Primary Examiner*—Alton D. Rollins
*Assistant Examiner*—Mark L. Berch
*Attorney, Agent, or Firm*—Bacon & Thomas

[57] ABSTRACT

Compounds of the general formula:

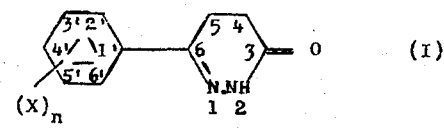

in which X represents a straight or branched chain alkyl or alkoxy group, a hydroxymethyl group, a cycloalkyl group, a cycloalkoxy group, an aryloxy group, a hydroxyl group, a fluorine atom, a chlorine atom, an amino or substituted amino group, a piperidino group, a morpholino group, a pyrrolidino group, a 1,2,3,6-tetrahydropyridino group, a 4-[3-azabicyclo(3,2,2)-nonyl] group, or a 4-(piperazin-1-yl) or 4-(4-substituted-piperazin-1-yl) group of the formula

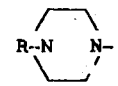

in which R=H, lower alkyl or 1–5 carbon atoms, aryl, substituted aryl, aralkyl, cinnamyl, acyl, ethoxycarbonyl, aroyl or substituted aroyl and n is an integer from 1 to 5 except that when n is 1 X is not an alkyl group of 1 to 3 carbon atoms or an alkoxy group of 1 or 2 carbon atoms or a chlorine atom in the 4'-position, or an amino or acylated amino group in positions 2', 3' or 4'; and when $n = 2$ the groups X cannot both be methyl or both be methoxy in the 2' and 5' positions, nor can X be a chlorine atom in both the 2' and 4' positions or the 3' and 4' positions, and when $n = 3$, X cannot all three be methoxy. These compounds have anti-hypertensive activity.

3 Claims, No Drawings

PYRIDAZINONES

This is a continuation of application Ser. No. 225,270, filed Feb. 10, 1972, now abandoned.

This invention relates to novel pyridazinones and to a process for the production thereof and to pharmaceutical compositions containing such pyridazinones.

We have found, according to the invention, that certain pyridazinones have an anti-hypertensive activity which is in some cases quite marked and is not associated with as many side reactions as may be encountered with known anti-hypertensive drugs.

The invention provides compounds of the general formula:

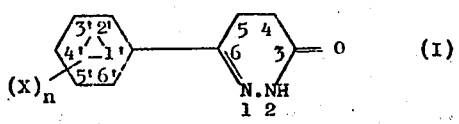

in which X represents a straight or branched chain alkyl or alkoxy group, a hydroxymethyl group, a cycloalkyl group, a cycloalkoxy group, an aryloxy group, a hydroxyl group, a fluorine atom, a chlorine atom, an amino or substituted amino group, a piperidino group, a morpholino group, a pyrrolidino group, a 1,2,3,6-tetrahydropyridino group, a 4-[3-azabicyclo(3,2,2)-nonyl] group, or a 4-(piperazin-1-yl) or 4-(4-substituted-piperazin-1-yl) group of the formula

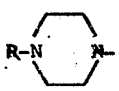

in which R=H, lower alkyl of 1–5 carbon atoms, aryl, substituted aryl, aralkyl, cinnamyl, acyl, ethoxy-carbonyl, aroyl or substituted aroyl and $n$ is an integer from 1 to 5 except that when $n$ is 1 X is not an alkyl group of 1 to 3 carbon atoms or an alkoxy group of 1 or 2 carbon atoms or a chlorine atom in the 4'-position, or an amino or acylated amino group in positions 2', 3' or 4' and when $n = 2$, the group X cannot both be methyl or both be methoxy in the 2' and 5' positions, nor can X be a chlorine atom in both the 2' and 4' positions or the 3' and 4' positions and when $n = 3$, X cannot all three be methoxy.

A preferred sub-class of compounds are those in which X is piperidino or morpholino or an alkoxy group containing from 1 to 12 carbon atoms, subject to the proviso specified above. Specific preferred compounds according to the invention are those the preparation of which is described in the Examples. Particularly preferred compounds are the following:

6-(o-methoxyphenyl)-4,5-dihydro-3(2H)-pyridazinone, (Example 1),
6-(p-piperidinophenyl)-4,5-dihydro-3(2H)-pyridazinone (Example 2),
6-(p-morpholinophenyl)-4,5-dihydro-3(2H)-pyridazinone (Example 3),
6-(o-ethoxyphenyl)-4,5-dihydro-3(2H)-pyridazinone (Example 7), and
6-(p-hexyloxyphenyl)-4,5-dihydro-3(2H)-pyridazinone, (Example 8).

Of these compounds the second mentioned and the last mentioned are particularly useful.

The compounds according to the invention may be prepared by a number of processes. In one process the parent 3-substituted benzoylpropionic acid II may be heated with hydrazine hydrate as indicated below

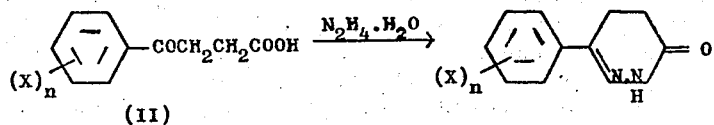

This reaction may be carried out by heating the components together preferably in solution under suitable conditions for example under reflux and recovering the product by cooling when the product crystallizes and can be separated off and if desired recrystallised.

In an alternative process, for the production of compounds in which X represents an alkoxy group the parent hydroxyphenyl pyridazinone can be alkylated directly using an alkylating agent such as alkyl halide in the presence of an acid binding agent, as follows:

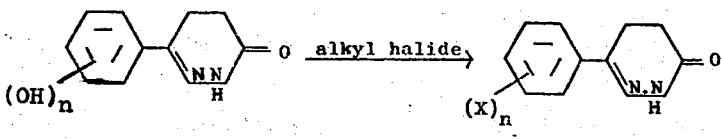

This alkylation may conveniently be carried out by heating the hydroxyphenyl compound with the alkylating agent under conditions of reflux in the presence of an acid binding agent. Suitable alkylating agents include for example 1-bromopropane, 1-bromohexane, 1-iodo-3-methylbutane and similar alkyl halides. Suitable acid binding agents include alkali metal hydroxides or carbonates such as potassium carbonate.

As will be appreciated the hydroxyphenyl pyridazinone is a compound according to the invention and accordingly the second process represents a subsequent conversion of the first (I; X=OH). Similarly 3-(p-substituted benzoyl) propionic esters of the acids II in which X represents a basic or heterocyclic moiety may be prepared from esters of the acids (II; X=p-fluoro) by reaction of such compounds with the appropriate base or heterocyclic base.

The parent acid II used as starting material may be prepared by a number of methods including for example the Friedel Crafts reaction between the appropriate substituted phenyl ether and succinic anhydride, reaction of a phenol with succinic anhydride and aluminium chloride, demethylation of the p-methoxy acid, reaction of the dialkoxybenzene with succinic anhydride and aluminium chloride and reaction of fluorobenzene with the same reagents. These reactions are appropriate to the production of the ortho- and/or para-acids. The meta-acids may be prepared by standard methods starting with the nitration of 3-p-benzoylpropionic acid to yield the m nitro acid, which may be reduced to the m-amino acid, diazotised to yield the m-chloro acid or the m-hydroxy acid which latter may be alkylated to the m-alkoxy acid.

The compounds according to the invention may be formulated for administration in association with a pharmaceutically acceptable carrier and the invention extends to such pharmaceutical compositions. The pharmaceutical compositions may be in any desired form and may be liquid, semi-solid or solid. As a liquid it may be in the form of an injectable solution wherein the carrier is sterile, non-pyrogenic water. It may also be in the form of a liquid for oral administration e.g. as an elixir or syrup which may contain adjuvants usual in such formulations. It may also be formulated as a capsule. The composition may also be in solid form, a particularly preferred form of administration being as a tablet. A suitable dose of the active compound is from 20 to 200 mg. per day and the pharamaceutical composition may be so formulated as to provide the whole or a proportion of such dose in a single dosage unit.

The following Examples illustrate the invention:

EXAMPLE 1

6-(p-Cyclopentylphenyl)-4,5-dihydro-3(2H)-pyridazinone

A solution of 3-(p-cyclopentylbenzoyl)propionic acid (4.9 g.) in warm ethanol (50 ml.) was treated with hydrazine hydrate (1.1 g.) and the mixture heated on the steam bath for 1 hour. The colourless crystalline material which separated, was collected and recrystallised from ethanol to yield the product (4.2 g.) in large, colourless needles, m.p. 191°–192°C.

Similarly obtained by the reaction of the appropriately substituted benzoyl propionic acid with hydrazine hydrate were:

6-(p-Phenoxyphenyl)-4,5-dihydro-3(2H)-pyridazinone m.p. 147°–148°C 6-(p-Cyclohexylphenyl)-4,5-dihydro-3(2H)-pyridazinone m.p. 201°–203°C 6-(p-Hydroxyphenyl)-4,5-dihydro-3(2H)-pyridazinone m.p. > 300°C 6-(o-Hydroxyphenyl)-4,5-dihydro-3(2H)-pyridazinone m.p. 216°–217°C 6-(p-Butoxyphenyl)-4,5-dihydro-3(2H)-pyridazinone m.p. 136°–137°C 6-(p-Fluorophenyl)-4,5-dihydro-3(2H)-pyridazinone m.p. 196°–198°C 6-(o-Methoxyphenyl)-4,5-dihydro-3(2H)-pyridazinone m.p. 120°–122°C 6-(m-Hydroxyphenyl)-4,5-dihydro-3(2H)-pyridazinone m.p. 260°–263°C 6-(m-Methoxyphenyl)-4,5-dihydro-3(2H)-pyridazinone m.p. 129°–131°C 6-(3,4-Dimethoxyphenyl)-4,5-dihydro-3(2H)-pyridazinone m.p. 169°–170°C 6-(3,4-Dihydroxyphenyl)-4,5-dihydro-3(2H)-pyridazinone m.p. 305°C (with decomposition)

6-(2,5-Dihydroxyphenyl)-4,5-dihydro-3(2H)-pyridazinone m.p. 289°–291°C 6-(2-Hydroxy-5-methoxyphenyl)-4,5-dihydro-3(2H)-pyridazinone m.p. 198°–200°C 6-(2-Hydroxy-4-methylphenyl)-4,5-dihydro-3-(2H)-pyridazinone m.p. 209°–210°C 6-(2-Methoxy-4-methylphenyl)-4,5-dihydro-3(2H)-pyridazinone m.p. 142°–143°C

EXAMPLE 2

6-(p-Piperidinophenyl)-4,5-dihydro-3(2H)-pyridazinone a. Methyl 3-(p-fluorobenzoyl)propionate A solution of 3-(p-fluorobenzoyl)propionic acid (58.8 g.) in anhydrous methanol (250 ml.) was treated with concentrated sulphuric acid (3.2 ml.) and the mixture heated at reflux temperature for 10 hours. It was then concentrated to a volume of 100 ml., cooled and diluted with ice-water. The resultant solid was collected and crystallised from ligroin to yield the ester (59.7 g.), m.p. 48°–50°C.

b. Methyl 3-(p-piperidinobenzoyl)propionate

A solution of the foregoing ester (42.0 g.) in dimethylsuphoxide (150 ml.) was treated with piperidine (17.0 g.), followed by anhydrous potassium carbonate (27.6 g) and the mixture was stirred and heated at 100°C for 30 hours. It was then cooled and poured into ice-water (1 litre) and the solid which precipitated was collected, washed well with cold water and dried (Yield 51.7 g, m.p. 67°–69°C). It was purified by crystallisation from methanol to yield the basic ester in fine pale, lemon-yellow needles, m.p. 72°–73°C.

c. 3-(p-Piperidinobenzoyl)propionic acid

A solution of the foregoing ester (20 g.) in ethanol (100 ml.) was treated with a solution of sodium hydroxide (4.0 g.) in water (100 ml.) and the mixture was heated at reflux temperature for 6 hours. It was then concentrated to half bulk to remove most of the ethanol, diluted with water (150 ml.), cooled and extracted with ether to remove any unchanged ester. The aqueous layer was adjusted to pH 4–5 by the addition of dilute (3N) hydrochloric acid and the precipitated solid was collected and washed with ice-cold water. It was crystallised from aqueous ethanol to yield the acid (17 g.), m.p. 150°–151°C.

d. 6-(p-Piperidinophenyl)-4,5-dihydro-3(2H)-pyridiazinone

A solution of 3-(p-piperidinobenzoyl)propionic acid (7.1 g) in ethanol (65 ml.) was treated with hydrazine hydrate (1.5 g.) and the mixture heated at reflux temperature for 3 hours. It was then cooled and the solid collected and washed with a little cold ethanol. It was crystallised from a mixture of ethanol and 1,2-dichlorethane to yield the title product (5 g.), m.p. 242°–244°C.

The product was obtained in smaller yield when methyl-3-(p-piperidinobenzoyl)propionate (5.5 g.) and hydrazine hydrate (1.1 g.) were heated in ethanol (50 ml.) at reflux temperature for 3 hours.

EXAMPLE 3

6-(p-Morpholinophenyl)-4,5-dihydro-3(2H)-pyridazinone a. Methyl 3-(p-morpholinobenzoyl)propionate

A solution of methyl 3-(p-fluorobenzoyl) propionate (42.0 g.) in dimethylsulphoxide (150 ml.) was treated with morpholine (17.4 g.) followed by anhydrous potassium carbonate (27.6 g.) and the mixture was stirred and heated at 100°C for 30 hours. It was then cooled, poured into ice-water (1 litre) and the precipitated solid collected, washed with cold water and dried. It was crystallised twice from methanol to yield the ester (23.1 g), m.p. 120°–121°C.

b. 3-(p-Morpholinobenzyl)propionic acid

A solution of the foregoing ester (19.4 g.) in ethanol (100 ml.) was treated with a solution of sodium hydroxide (4.0 g.) in water (100 ml.) and the mixture heated at reflux temperature for 6 hours. It was concentrated to about one third bulk, diluted with water (150 ml.) and extracted with ether to remove any unchanged ester. The aqueous layer was adjusted to pH 2 by addition of 3N hydrochloric acid when precipitation occurred. The solid was collected, washed with cold water and dried. Cyrstallisation from ethanol furnished the pure acid (15.5 g.), m.p. 167°–168°C.

c. 6-(p-Morpholinophenyl)-4,5-dihydro-3(2H)-pyridazinone

A solution of 3-(p-morpholinobenzoyl)propionic acid (11.7 g.) in warm ethanol (150 ml.) was treated with hydrazine hydrate (2.5 g.) and the mixture heated at reflux temperature for 4 hours. It was then cooled and the solid collected (11.0 g; m.p. 226°–229°C). This was crystallised from a mixture of ethanol (100 ml.) and 1,2-dichloroethane (150 ml.) to yield the product as colourless needles, m.p, 225°–228°C.

Similarly prepared by the reaction of an appropriate amine with methyl 3-(p-fluorobenzoyl)propionate followed by hydrolysis and treatment with hydrazine hydrate were:

6-[p-(3-Azabicyclo[3,2,2]-nonylphenyl]-4,5-dihydro-3(2H)-pyridazinone m.p. 273°–275°C
6-[p-(4-Methylpiperazinyl)phenyl]-4,5-dihydro-3(2H)-pyridazinone hemihydrate m.p. 223°–224°C.
6-[p-(1,2,3,6-Tetrahydropyridino)phenyl]-4,5-dihydro-3(2H)-pyridazinone m.p. 222°–228°C (with decomposition)
6-[p-Pyrrolidinophenyl)-4,5-dihydro-3(2H)-pyridazinone m.p. 296°C (with decomposition
6-[p-(4Benzylpiperazin1-yl)phenyl]-4,5-dihydro-3(2H)pyradazinone m.p. 180°–182°C.
6-[p-(4-Benzoylpiperazin-1-yl)phenyl]-4,5-dihydro-3(2H)-pyridazinone m.p. 264°–265°C
6-[p-(4-phenethylpiperazin-1-yl]-4,5-dihydro-3(2H)-pyridazinone m.p. 255°–257°C
6-[p-(4-Phenylpiperazin-1-yl)phenyl]-4,5-dihydro-3(2H)-pyridazinone m.p. 296°–297°C
6-[p-(4-Ethoxycarbonylpiperazin-1-yl)phenyl]-4,5-dihydro-3(2H)-pyridazinone m.p. 221°–222°C
6-[p-(4-o-Methoxyphenylpiperazin-1-yl)phenyl]-4,5-dihydro-3(2H)-pyridazinone m.p. 217°–218°C
6-[p-(4-p-Methoxyphenylpiperazin-1-yl)phenyl]-4,5-dihydro-3(2H)-pyridazinone m.p. 264°–266°C
6-[p-(4-p-Tolylpiperazin-1-yl)phenyl]-4,5-dihydro-3(2H)-pyridazinone m.p. 268°–270°C.
6-[p-(4-o-Ethoxyphenylpiperazin-1-yl)phenyl]-4,5-dihydro-3(2H)-pyridazinone m.p. 218°–219°C.
6-[p-(4-Ethylpiperazin-1-yl)phenyl]-4,5-dihydro-3(2H)-pyridazinone m.p. 224°–225°C.
6-[p-(4-Pentylpiperazin-1-yl)phenyl]-4,5-dihydro-3(2H)-pyridazinone m.p. 184°–185°C.

EXAMPLE 4

6-(p-Propoxyphenyl)-4,5-dihydro-3(2H)-pyridazinone a. Ethyl-3-(p-propoxybenzoyl)propionate

To a solution of ethyl 3-(p-hydroxybenzoyl propionate (31.0 g.) in acetone (300 ml.) was added anhydrous potassium carbonate (15.2 g.) and 1-bromopropane (17.2 g.) and the mixture was heated at reflux temperature for 12 hours. It was then cooled, poured into ice-waater (1 litre) and the oil isolated with methylene dichloride. It was purified by distillation at reduced pressure and had bp 168°–170° at 0.2 mm; $n_D^{24.5}$ = 1.5200.

b. 3-(p-propoxybenzoyl)propionic acid

This was prepared in 90% yield by hydrolysis of the foregoing ester with sodium hydroxide in aqueous ethanol and had mp 116°–117°C.

c. 6-(p-Propoxyphenyl)-4,5-dihydro-3(2H)-pyridazinone

This was prepared in 83% yield by reaction of the foregoing acid with hydrazine hydrate as described in the earlier Examples and had mp 154°–155°C after crystallisation from ethanol.

Similarly prepared by the reaction of the appropriate alkyl halide with ethyl 3-(p-hydroxybenzoyl) propionate followed by hydrolysis and treatment with hydrazine hydrate were:

6-(p-Isopropoxyphenyl)-4,5-dihydro-3(2H)-pyridazinone m.p. 174°–175°C
6-[p-(3-Methylbutoxy)phenyl]-4,5-dihydro-3(2H)-pyridazinone m.p. 126°–127°C
6-(p-Hexyloxyphenyl)-4,5-dihydro-3(2H)-pyridazinone m.p. 110°–111°C
6-[p-(1-Ethylpropoxy)phenyl]-4,5-dihydro-3(2H)-pyridazinone m.p. 127°–128.5°C
6-(p-n. Octyloxyphenyl)-4,5-dihydro-3(2H)-pyridazinone m.p. 120°–121°C
6-(p-n. Nonyloxyphenyl)-4,5-dihydro-3(2H)-pyridazinone m.p. 125°–126.5°C
6-(p-Decyloxyphenyl)-4,5-dihydro-3(2H)-pyridazinone m.p. 130°–132°C
6-[p-(1-Ethylbutoxy)phenyl]-4,5-dihydro-3(2H)-pyridazinone m.p. 109°–111°C
6-(p-Dodecyloxyphenyl)-4,5-dihydro-3(2H)-pyridazinone m.p. 165°–135°C
6-(p-Heptyloxyphenyl)-4,5-dihydro-3(2H)-pyridazinone m.p. 106°–107°C

EXAMPLE 5

6-(p-Propoxyphenyl)-4,5-dihydro-3(2H)-pyridazinone

A solution of 6-(p-hydroxyphenyl)-4,5-dihydro-3(2H)-pyridazinone (7.7 g.), in ethanol (80 ml. containing sodium hydroxide (1.7 g.) was treated with 1-bromopropane (5.4 g.) and the mixture was heated at reflux temperature for 2½ hours. The solid which separated on cooling was collected and recrystallised from ethanol to yield the pyridazinone (4.4 g.), m.p.

154°–155°C. The product was identical with that prepared by an alternative route (Example 4).

EXAMPLE 6

6-(p-Cyclohexyloxyphenyl)-4,5-dihydro-3(2H)-pyridazinone a. 3-(p-Cyclohexyloxybenzoyl)propionic acid A solution of succinic anhydride (20 g.) and phenoxycyclohexane (35.1 g.) in 1,2-dichloroethane (250 ml.) was stirred at 0°C and treated with powdered anhydrous aluminium chloride (58.2 g.) and stirring was continued for 5 hours at 0°–5°C. It was then poured carefully with stirring into ice-water (1 liter) containing concentrated hydrochloric acid (100 ml.). The organic layer was separated, washed with water and extracted with a solution of sodium hydroxide (8 g.) in water (250 ml.). The alkaline extract was adjusted to pH 4–6 by the addition of dilute hydrochloric acid to yield the product (6.8 g.), m.p. 190°–192°C after crystallisation from aqueous methanol.

b. 6-(p-Cyclohexyloxyphenyl)-4,5-dihydro-3(2H)-pyridazinone

This was prepared in 80% yield by reaction of the foregoing acid with hydrazine hydrate in ethanol at reflux temperature for 4 hours. It had m.p. > 300°C after crystallisation from a mixture of ethanol (2 volumes) and isopropanol (1 volume).

Similarly prepared by reaction of the appropriate phenyl ether with succinic anhydride followed by treatment with hydrazine hydrate were:

6-(p-Pentyloxyphenyl)-4,5-dihydro-3(2H)-pyridazinone m.p. 124°–126°C
6-(p-Hexyloxyphenyl)-4,5-dihydro-3(2H)-pyridazinone m.p. 110°–111°C.

EXAMPLE 7

6-(o-Ethoxyphenyl)-4,5-dihydro-3(2H)-pyridazinone a. Ethyl 3-(o-hydroxybenzoyl)propionate A solution of 3-(o-hydroxybenzoyl)propionic acid (18.8 g.) in ethanol (120 ml.) was treated with concentrated sulphuric acid (1 ml.) and the mixture heated at reflux temperature for 12 hours. It was cooled, poured into ice-water (350 ml.) and the oily solid isolated with chloroform. It (18.6 g.) was purified by distillation at reduced pressure and had bp 112°–113°C at 0.1 mm; $n_D^{24.5} = 1.5301$.

b. Ethyl-3-(o-ethoxybenzoyl)propionate

This was prepared in 58% yield by alkylation of the foregoing ester with ethyl bromide in ethanolic solution in the presence of 1 equivalent of potassium hydroxide. It has bp 135–136°C at 0.15 mm; $n_D^{32.5} = 1.5119$.

c. 3-(o-Ethoxylbenzoyl)propionic acid

This was prepared in 80% yield by hydrolysis of the foregoing ester with sodium hydroxide in 50% aqueous ethanol and had mp 125°–127°C after crystallisation from aqueous ethanol.

d. 6-(o-Ethoxyphenyl)-4,5-dihydro-3(2H)-pyridazinone

This was obtained in 88% yield by reaction of 3-(o-ethoxybebzoyl)propionic acid with hydrazine hydrate at reflux temperature for 6 hours, and had m.p. 137°–139°C after crystallisation from ethanol.

Similarly prepared using hexyl bromide in place of ethyl bromide was: 6-(o-Hexyloxyphenyl)-4,5-dihydro-3(2H)-pyridazinone m.p. 75°–77°C.

EXAMPLE 8

6-(3-Amino-4-methoxyphenyl)-4,5-dihydro-3(2H)-pyridazinone a. 3-(3-Amino-4-methoxybenzoyl)propionic acid A solution of 3-(4-methoxy-3-nitrobenzoyl) propionic acid (10.5 g.) in 5N ammonia solution (150 ml.) was added in one portion to a stirred hot (90°C) solution of hydrated ferrous sulphate (90 g.) in water (210 ml.) and stirring was continued for 10 minutes more. The hot mixture was filtered through Hyflo and the filtrate was concentrated to 50 ml. volume and neutralised with acetic acid. The mixture was cooled, the precipitated solid collected and purified by crystallisation from dilute methanol to yield the amine, (5.5 g.), m.p. 136°–137°C.

b. 6-(3-Amino-4-methoxyphenyl)-4,5-dihydro-3(2H)-pyridazinone

This was prepared in 95% yield by reaction of 3-(3-amino-4-methoxybenzoyl)-propionic acid with hydrazine hydrate in ethanolic solution at reflux temperature for 5 hours. It had m.p. 218°–220°C after crystallisation from ethanol.

EXAMPLE 9

6(3-Chloro-4-methoxyphenyl)-4,5-dihydro-3(2H)-pyridazinone a. 3-(3-Chloro-4-methoxybenzoyl)propionic acid A solution of 3-(3-amino-4-methoxybenzoyl) propionic acid (5 g.) in concentrated hydrochloric acid (25 ml.) was diazotised at 0°C by the addition of a solution of sodium nitrite (1.54 g.) in water (5 ml.). This diazo solution was added with stirring to a solution containing hydrated copper sulphate (6.3 g.) and sodium chloride (5.4 g.) in water (20 ml.) to which had been added a solution containing sodium metabisulphite (1.4 g.) and sodium hyroxide (0.9 g.) in water (10 ml.). The mixture was then heated on the steam bath for 30 minutes when a solid separated. The mixture was cooled, the solid collected and washed with cold water. It was crystallised from methanol to yield the product (4.2 g.), m.p. 187°–189°C.

b. 6-(3-Chloro-4-methoxyphenyl)-4,5-dihydro-3(2H)-pyridazinone

This compound was prepared in 84% yield by reaction of 3-(3-chloro-4-methoxybenzoyl)propionic acid with hydrazine hydrate in ethanolic solution at reflux temperature for 5 hours. It had mp 194°–195°C after crystallisation from ethanol.

EXAMPLE 10

6-(3-Acetamido-4-methoxyphenyl)-4,5-dihydro-3(2H)-pyridazinone a. 3-(3-Acetamido-4-methoxybenzoyl)propionic acid A mixture of 3-(3-amino-4-methoxybenzoyl) propionic acid (15.61 g.) with acetic anhydride (7.14 g.) was treated with concentrated sulphuric acid (2 drops) and heated on the steam bath for 3 hours. It was then cooled and decomposed by the addition of ice. The resultant solid was collected and crystallised from methanol to yield the product, (10.5 g.), m.p. 184°–185°C.

b. 6-(3-Acetamido-4-methoxyphenyl)-4,5-dihydro-3(2H)-pyridazinone

This was obtained in 90% yield by reaction of 6-(3-acetamido-4-methoxybenzoyl)-propionic acid with hydrazine hydrate in ethanolic solution at reflux temperature for 5 hours, and had m.p. 240°–241°C after crystallisation from ethanol.

EXAMPLE 11

6-(4-Hydroxy-3-methoxyphenyl)-4,5-dihydro-3(2H)-pyridazinone a. 3-(4-Hydroxy-3-methoxybenzoyl)propionic acid

Guaiacol hydrogensuccinate (11.2 g.) was added to a suspension of anhydrous aluminium chloride (15.5g.) in 1,2-dichloroethane (30 ml.) and the mixture was heated at reflux temperature for 24 hours. It was then cooled and poured into a mixture of ice and hydrochloric acid, the organic layer was removed and the residual solid material crystallised from dilute methanol to give the product (5 g.), m.p. 174°–175°C.

b. 6-(4-Hydroxy-3-methoxyphenyl)-4,5-dihydro-3(2H)-pyridazinone

This was obtained in 95% yield when the foregoing acid was heated with hydrazine hydrate in ethanolic solution for 5 hours. It had m.p. 209°–210°C after crystallisation from ethanol.

EXAMPLE 12

6-(3-Hydroxymethyl-4-methoxyphenyl)-4,5-dihydro-3(2H)-pyridazinone a. Methyl 3-(3-chloromethyl-4-methoxybenzoyl)propionate

A solution of methyl 3-(4-methoxybenzoyl) propionate (40 g.) in chloroform (100 ml.) was treated with paraformaldehyde (15 g.) and anhydrous zinc chloride (10 g.). It was then cooled to -4°–0°C, stirred and a slow stream of hydrogen chloride was passed into the mixture until it was saturated. Stirring was continued for a further 30 minutes at room temperature when the mixture was poured into cold water and the organic layer was isolated, washed thoroughly with cold water and dried over anhydrous sodium sulphate. The solvent was distilled off and the resultant solid purified by crystallisation from methanol. It (25 g.) had m.p. 78°–80°C.

b. 3-(3-Hydroxymethyl-4-methoxybenzoyl)propionic acid

The foregoing chloromethyl compound (6.75 g.) was heated with a solution of potassium hydroxide (5.6 g.) in water (30 ml.) at 100° for 4 hours. It was then cooled and acidified to Congo red by the addition of hydrochloric acid. The resultant solid was crystallised from methanol to yield the product (2.1 g.), m.p. 217°–218°C.

c. 6-(3-Hydroxymethyl-4-methoxyphenyl)-4,5-dihydro-3(2H)-pyridazinone

A solution of the foregoing acid (2.38 g.) in ethanol (120 ml.) was treated with hydrazine hydrate (1.1 g.) and the mixture heated at reflux temperature for 5 hours. The product crystallised on cooling and had m.p. 207°–208°C after recrystallisation from ethanol. Yield (1.2 g.).

EXAMPLE 13

6-(p-Piperazin-1-yl)phenyl-4,5-dihydro-3(2H)-pyridazinone hydrochloride a. Methyl 3-[p-(4-ethoxycarbonylpiperazin-1-yl)benzoyl] propionate

This ester was prepared in 43% yield by reaction of methyl 3-(p-fluorobenzoyl) propionate with 1-ethoxycarbonyl piperazine in dimethylsulphoxide in the presence of potassium carbonate at 100°C for 30 hours. It had m.p. 119°–120°C (from methanol).

b. 3-(4-Piperazin-1-yl)benzoylpropionic acid hydrochloride

This acid was prepared by hydrolysis of the foregoing ester with 2 mole equivalents of sodium hydroxide in 50% aqueous ethanol followed by concentration and acidification with hydrochloric acid. It was obtained in 67% yield and had m.p. 255°–256°C (from methanol).

c. 6-(p-Piperazin-1-yl)phenyl-4,5-dihydro-3(2H)-pyridazinone hydrochloride

The title compound was obtained in theoretical yield by reaction of the foregoing acid hydrochloride with 2 mole equivalents of hydrazine hydrate in ethanolic solution at reflux temperature for 5 hours. It had m.p. 326°–327°C (with decomposition) (From 2-methoxyethanol).

EXAMPLE 14

6-(2,4-Diethoxyphenyl)-4,5-dihydro-3(2H)-pyridazinone a. 3-(2,4-Diethoxybenzoyl)propionic acid

A mixture of m-diethoxybenzene (22 g.) and succinic anhydride (15 g.) was dissolved in 1,2-dichloroethane and the resultant solution was stirred and treated with powdered aluminum chloride (30 g.), added gradually during 1 hour with external cooling to keep the reaction temperature at 10°C. The reaction mixture was stirred for 1 hour further, poured into water and the solvent was boiled off. The remaining oily suspension crystallized on stirring and cooling and the solid was collected and dried (Yield 15.5 g.). It has m.p. 139°–141°C after crystallisation from toluene.

b. 6-(2,4-Diethoxyphenyl)-4,5-dihydro-3-(2H)-pyridazinone

A solution of the foregoing acid (8.0 g.) in hot ethanol (80 ml.) was treated with hydrazine hydrate (1.8 ml.) and the solution was heated at reflux temperature for 4 hours. The product, which separated when the reaction mixture cooled, was collected and washed with methanol. It had m.p. 148°–150°C after crystallisation from ethanol (Yield 5.5 g.).

EXAMPLE 15

6-(o-Propoxyphenyl)-4,5-dihydro-3(2H)-pyridazinone a. 3-(o-Propoxybenzoyl)propionic acid 3-(o-Hydroxybenzoyl)propionic acid (14.6 g.) was dissolved in n-butanol (300 ml.) containing 85% potassium hydroxide (10 g.) and the resultant solution was treated with 1-bromopropane (24.6 g.) and the mixture heated at reflux temperature for 4 hours. It was then cooled, filtered to remove potassium bromide and the filtrate washed with cold water. The butanol was evaporated at reduced pressure and the residual oil distilled at 0.3 mm when the fraction b.p. 160°–180°C was collected (16.4 g.). This was dissolved in methanol (50 ml.), treated with 20% sodium hydroxide solution (20 ml.) and heated on the steambath for 30 minutes. The methanol was boiled off and the residue diluted with water (250 ml.) and acidified with hydrochloric acid. The precipitated acid was collected and crystallised from 50% methanol. It had m.p. 77°–79°C (Yield 13.3 g.).

b. 6-(o-Propoxyphenyl)-4,5-dihydro-3(2H)-pyridazinone

This was obtained in 90% yield by reaction of the foregoing acid with hydrazine hydrate as described in earlier Examples. It had m.p. 117.5°–119.5°C after crystallisation from aqueous methanol.

Similarly 6-(o-Pentyloxyphenyl)-4,5-dihydro-3(2H)-pyridazinone (m.p. 50°–52°C after crystallisation from aqueous methanol) was prepared from 1-bromopentane in place of 1-bromopropane.

What is claimed is:

1. A compound of the formula:

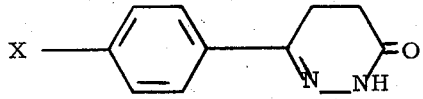

wherein X is: a straight or branched chain alkoxy group having 3-12 carbon atoms.

2. The compound of claim 1 wherein the alkoxy group is selected from the group consisting of propoxy, isopropoxy, methylbutoxy, butoxy, ethylpropoxy, hexyloxy, octyloxy, nonyloxy, decyloxy, ethylbutoxy, dodecyloxy, heptyloxy and pentyloxy.

3. The compound of claim 1 which is 6(p-hexyloxyphenyl)-4,5-dihydro-3(2H)-pyridazinone.

* * * * *